United States Patent [19]
Tobia

[11] Patent Number: 5,651,360
[45] Date of Patent: Jul. 29, 1997

[54] PEEP CONTROL FOR BELLOWS VENTILATOR

[75] Inventor: Ronald L. Tobia, Sun Prairie, Wis.

[73] Assignee: Ohmeda Inc., Liberty Corner, N.J.

[21] Appl. No.: 624,067

[22] Filed: Mar. 29, 1996

[51] Int. Cl.$^6$ .................................................. A61M 16/00
[52] U.S. Cl. ............................. 128/204.28; 128/205.24
[58] Field of Search ......................... 128/204.28, 205.13,
128/205.24, 205.29, 910; 137/494, 906,
87, 115.13, 115.18, 115.24; 251/61, 61.1

[56] References Cited

U.S. PATENT DOCUMENTS

| | | | |
|---|---|---|---|
| 4,838,257 | 6/1989 | Hatch | 128/204.18 |
| 5,315,989 | 5/1994 | Tobia | 128/204.28 |

Primary Examiner—Vincent Millin
Assistant Examiner—Robert N. Wieland
Attorney, Agent, or Firm—Roger M. Rathburn; R. Hain Swope; Salvatore P. Pace

[57] ABSTRACT

An improved system for the control of PEEP in a medical ventilator system having a ventilator and a bellows contained within a bellows canister. A pop-off valve that normally vents excess pressure within the bellows to atmosphere is modified such that its exhaust is vented to a predetermined pressure above atmospheric pressure, such as the PEEP pressure. In the preferred embodiment, that predetermined pressure is the pressure within the ventilator drive gas conduit that transmits the gas from the ventilator to drive the bellows and the exhaust from the pop-off is effectively isolated from that drive gas conduit to avoid contaminating the gas within that drive gas conduit.

16 Claims, 3 Drawing Sheets

5,651,360

PEEP CONTROL FOR BELLOWS VENTILATOR

BACKGROUND OF THE INVENTION

This invention relates to medical ventilators and, more particularly, to an improved system for controlling the positive end expiratory pressure in such ventilators.

In general, medical ventilator systems are used in the administration of anesthesia to a patient undergoing operations and to maintain the patient under anesthesia until the cessation of the operation. Such systems include ventilators to provide a breath to the patient and which typically include a bellows in the system to separate the breathing circuit to which the patient is connected from the drive gas emanating from the ventilator. This is normally done in order to allow the partial reuse of the breathing circuit gases on successive breaths from the patient.

An advantage of such rebreathing in anesthesia systems is that the rebreathing of the gases allows the reuse of the expensive anesthetic agents that are added to such breathing gases. Thus, utilization of the anesthetic agent is reduced and the cost of using such agent is minimized.

There are several types of bellows systems used with medical ventilators including the hanging type of bellows, driven bellows and standing bellows. Of these, the standing bellows is typically driven pneumatically by increasing the pressure within the bellows canister external of the bellows itself during the inhalation cycle by forcing gas from the ventilator into that canister. The bellows is thus forced in a downward direction (gravity added) by the ventilator, thereby expelling the gas from inside the bellows to the patient circuit to breathe the patient. During exhalation, the bellows is allowed to rise back to its original position when the ventilator drive pressure is released and as the patient exhales. Additional fresh gas is admitted to the system to assist in returning the bellows to its full up position.

In order to allow the bellows to rise against the force of gravity, an exhaust valve, commonly known as a pop-off valve, is employed which is biased closed and piloted by the ventilator drive pressure. When that ventilator drive pressure is released, the bellows rises so as to make contact with the top of the bellows canister. At this point, the pressure within the bellows rises rapidly as additional fresh gas is added to the system and reaches the point where the popoff valve is opened against the bias and releases the gases to the atmosphere.

Typically, a relatively small amount of fresh gas flow is continuously added to the breathing circuit so the exhaust of gases through the pop-off valve occurs towards the end of each patient exhalation. The exhaust gas from the pop-off valve is generally scavenged to an appropriate exhaust system in the hospital so that the local area is not contaminated with anesthetic laden gases.

In order to properly ventilate patients exhibiting some degree of respiratory compromise, clinicians frequently use a mode of ventilation called positive end expiration pressure (PEEP). In that mode of ventilation, a positive airway pressure is maintained during the exhalation phase of the patient's breath. Mechanical biased check valves (PEEP Valves) are commonly used within the expiratory side of the patient circuit in order to maintain the PEEP pressure. When the ventilator drive pressure is released, gas exits the pressurized portion of the breathing circuit through the mechanical PEEP valve and the drive pressure thereafter refills the bellows in the normal manner.

For safety and performance reasons, it is desirable to control the PEEP level electronically from the ventilator front panel. One technique for achieving this type of "electronic" PEEP control is to maintain a positive pressure in the ventilator drive circuit during exhalation. One ventilator that produces PEEP in this fashion is shown and described in U.S. Pat. No. 5,315,989 of Tobia, and which is assigned to the present assignee. The disclosure of that patent is incorporated herein by reference. Since the bellows pop-off valve is piloted by the drive pressure, a concomitant rise in the bellows base pressure will also occur. Once the bellows reaches the top of the canister, the pop-off valve bias is overcome and the valve exhausts into a near atmospheric (scavenging) pressure.

One problem with the release of that gas through the pop-off valve under the electronic control condition is that as the gas is released from a relatively high pressure to near atmospheric pressure, too much gas can be released from the pop-off valve causing the pressure within the bellows, breathing circuit and drive circuit to undershoot the desired PEEP pressure level. The cause is due to the pop-off valve relieving across a much higher and variable pressure than occurs without PEEP engaged.

When operating with active PEEP control systems, such as that described in the aforementioned Tobia U.S. Patent, once the PEEP undershoot occurs, the drive pressure is increased in order to reestablish the breathing circuit pressure at the PEEP level. That response serves to shut off the pop-off valve and possibly drive the bellows downwardly slightly. Eventually, the bellows refills with the continuing inflow of fresh gas and once again contacts the top of the bellows canister. As the pop-off valve reopens, the cycle is repeated, creating a sustained "limit cycle" oscillation condition. When operating with a passive PEEP control system, the breathing circuit maintains a constant pressure, but at an indeterminate amount below the PEEP level, also an undesirable outcome.

The aforesaid PEEP control problem can also occur when operating systems are in pressure ventilation mode. Depending on the ventilation parameters set by the clinician and those of the patient, the bellows may refill and engage the top of the bellows canister during the later stages of an inspiratory period. Similar limit cycle oscillations and undershoots to those previously described for PEEP can therefore occur during this portion of the breathing cycle.

SUMMARY OF THE INVENTION

The system of the present invention therefore corrects the aforedescribed problem connecting the exhaust from the bellows pop-off valve to a system of variable pressure, as opposed to atmospheric or near atmospheric pressure (scavenging pressure) typical of prior art systems. This allows the exhaust to be released in a more controlled fashion, preventing the undershoots of the target PEEP level.

One means of carrying out the present invention is to link the exhaust from the bellows pop-off valve to the drive pressure of the ventilator, thus controlling the release of both drive gas and bellows pop-off flow with the ventilator exhalation valve. The effect of the invention, therefore, is to raise the base pressure observed by the bellows and pop-off valve from atmospheric to a higher pressure resulting in the desired PEEP level being generated in the patient circuit. With the gas from the pop-off valve now regulated through the ventilator exhaust valve, the PEEP control problem is considerable simplified and improved PEEP regulation can be achieved.

In a preferred embodiment, gas from the bellows pop-off valve pneumatically communicates with the drive gas through a single interconnect conduit. With each breath, this interconnect is purged by the drive gas, thus preventing the gas released from the pop-off valve from mixing with gas in the ventilator drive line. This is desirable in that the gas emanating from the pop-off valve is dirty since it contains humidity as well as patient excretions from the patient exhalation.

Other objects, features and advantages of the present invention will be more readily apparent from the detailed description of the preferred embodiment set forth below, taken in conjunction with the accompanying drawings.

DESCRIPTION OF THE PREFERRED EMBODIMENT

Figure 1:
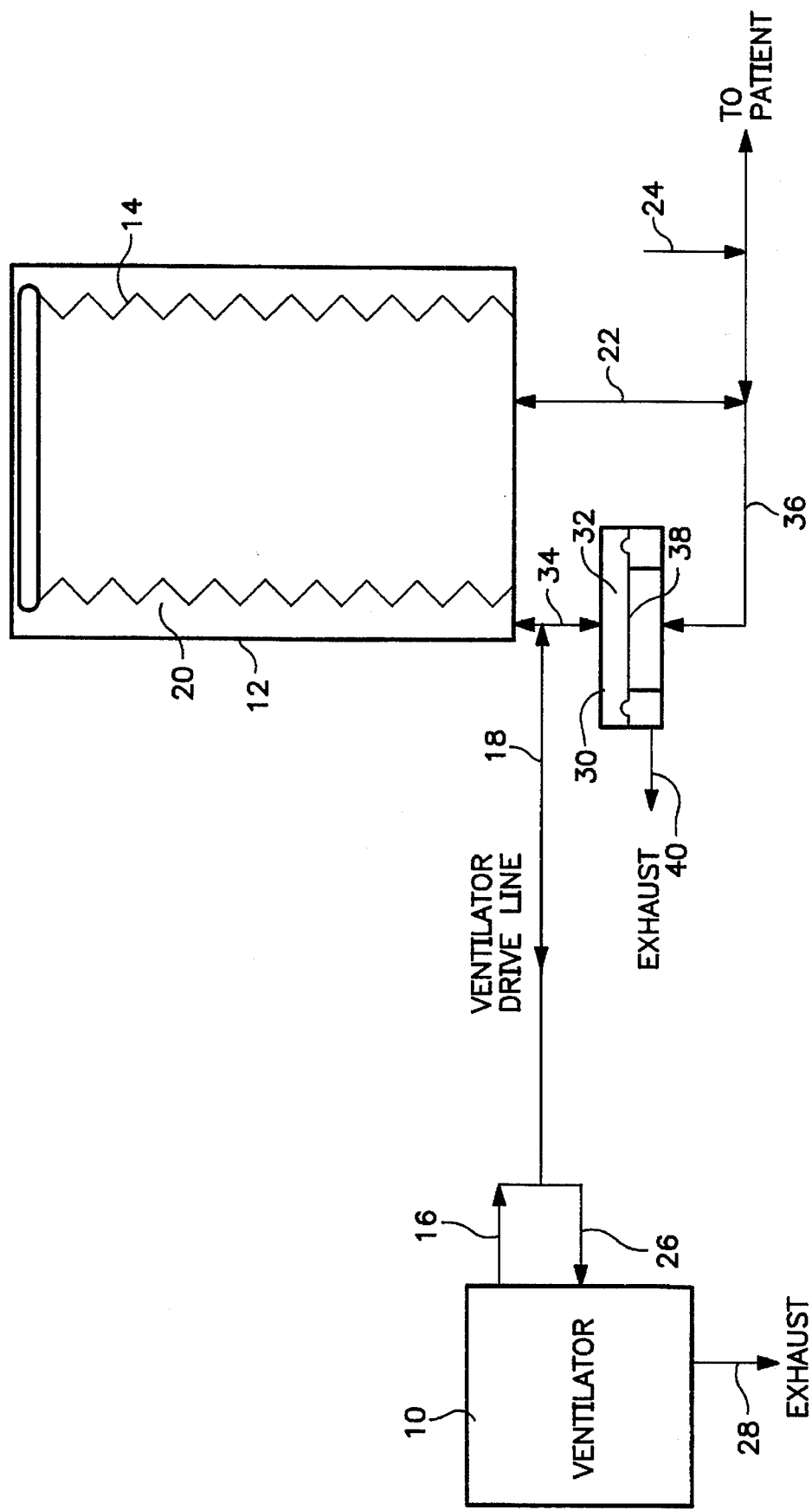
FIG. 1 is a schematic view of a ventilator and bellows system with a pop-off valve operating in accordance with the prior art.

Referring now to FIG. 1, there is shown a schematic view of a ventilator 10 and a bellows system that is typical of systems used in the prior art. Again, for completeness, reference is made to the aforementioned U.S. Pat. No. 3,515,989 of Tobia and which describes a ventilator system in considerable detail. In the present system, the bellows system includes a bellows canister 12 containing a flexible bellows 14 that contracts and expands within the canister 12 to provide a breath to the patient and to allow the patient to exhale.

As shown in FIG. 1, the ventilator 10 provides a flow of pressurized gas via a conduit 16 towards the ventilator drive line 18 and thus to the interior of the canister 12. Therefore, when the ventilator 10 is providing a breath to the patient, the gas from the ventilator 10 pressurizes the intermediate space 20 between the exterior of bellows 14 and the interior of canister 12, thereby causing the bellows 14 to compress as a breath is pushed into a patient circuit 22 and thus to the patient. As noted, the compression of the bellows 14 is aided by the force of gravity.

During exhalation, the pressure in the ventilator drive line 18 is relieved to atmospheric pressure and the patient's exhalation, aided by the introduction of fresh gas into the system at fresh gas inlet 24, causes the bellows 14 to reinflate to its upper position as shown in FIG. 1. Thus, during the exhalation, gas is expelled from the intermediate volume 20 and returns toward the ventilator 10 through the ventilator drive line 18 and thus proceeds to enter conduit 26 where the gas is released through an exhaust valve (not shown) within the ventilator 10 to the atmosphere through ventilator exhaust line 28.

When electronic PEEP is employed, a pressure is retained in the ventilator drive line 18 by the ventilator 10 and establishes a positive pressure which remains in the patient's lungs even at the end of the exhalation phase. This PEEP pressure may be from about 4 cm. $H_2O$ to about 30 cm. $H_2O$.

A bellows pop-off valve 30 is also conventionally provided in the system which relieves the excess pressure from the patient circuit and the internal space of the bellows 14 once the bellows has reached the top of the canister 12. As shown, the pop-off valve 30 includes a control chamber 32 that communicates via a conduit 34 with the ventilator drive line 18 and the intermediate space 20. The pop-off valve 30 is in communication with the patient circuit 22 by means of a conduit 36 and a diaphragm 38 is movable depending upon the differential pressure thereacross to relieve the patient circuit 22 to the atmosphere through a pop-off exhaust line 40.

As shown, that exhaust through pop-off exhaust line 40 relieves the patient circuit 22 directly to the atmosphere, however, the exhaust line 40 may conventionally be in communication with a hospital scavenging system to prevent the exhaust gas, which is contaminated by the patient's exhalation and anesthetic agent, from entering the hospital environment. Accordingly, while the exhaust line 40 may vent to atmosphere, often it will be exhausting into a scavenging pressure that is slightly negative relative to atmosphere.

As now can be seen, in the conventional system, the ventilator 10, during the inhalation cycle, supplies a breath of pressurized gas through the ventilator drive line 18 to pressurize the intermediate volume 20 internal of the canister 12, thereby causing the bellows 14 to compress and send a breath to the patient. That same pressurized gas that powers the bellows 14 also acts in the control chamber 32 against diaphragm 38 to maintain the pop-off valve 30 in the closed position.

In the exhalation cycle, the pressure in the ventilator drive line 18 is relieved via an exhalation valve, not shown, and the pressure within the intermediate volume 20 is relieved, allowing the patient to exhale. Thus the bellows 14 reinflates by means of the patients exhalation and via the addition of fresh gas at 24. When the bellows 14 reaches its upper position, its further movement is prevented and the pressure within the bellows 14 continues to increase, ultimately resulting in that pressure being vented through the pop-off valve 30 to atmospheric or scavenging pressure through pop-off exhaust line 40.

When closed loop controlled electronic PEEP is employed, there is a higher than normal differential pressure across the pop-off valve i.e. in the range of 4-30 cm. $H_2O$. This higher differential pressure causes a momentary uncontrolled burst of gas out of pop-off valve 30 causing a sufficient loss of volume so as to reduce the pressure in the interior of the bellows 14 below the PEEP level. As this occurs, the bellows 14 may deflate slightly allowing the pressure in the intermediate space 20 to momentarily decrease. The fresh gas returns the bellows 14 back to its fully inflated condition as the ventilator restores pressure in the ventilator drive line 18. Eventually, the pop-off valve 30 again vents the patient circuit 22 to atmosphere causing the same phenomena to reoccur, thereby creating unwanted "limit cycle" oscillations in the system.

Figure 2:
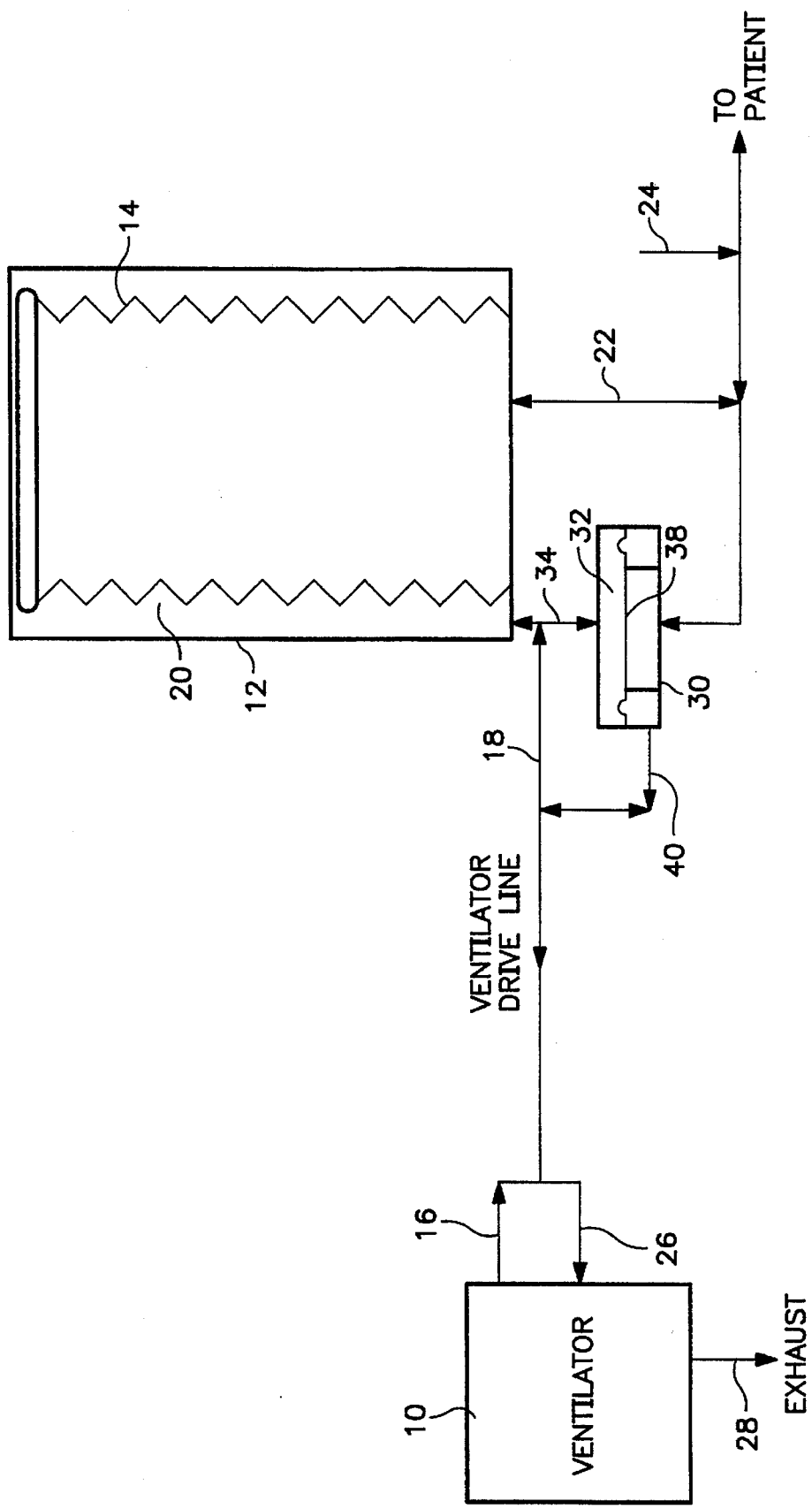
FIG. 2 is a schematic view of a ventilator and bellows system operating in accordance with the present invention.

Turning now to FIG. 2, there is shown a schematic view of a ventilator and bellows system constructed in accordance with the present invention. As can be seen in FIG. 2, the pop-off exhaust line 40 from the pop-off valve 30 has been connected to the drive ventilator line 18, thus the pop-off valve 30 does not exhaust to atmospheric pressure but, instead, exhausts to the pressure of the gas within the ventilator drive line 18. Thus the problem of overshooting the PEEP level is alleviated and all release of gas from within the system is accomplished through the ventilator exhalation valve. As the ventilator exhalation valve controls the pressure within drive line 18, the exhaust from the pop-off valve 30 can now also be effectively controlled.

Seen in another way, the effect of venting the pop-off valve exhaust into the drive pressure is to raise the base pressure observed by the bellows 14 and pop-off valve 30 from atmospheric to a higher pressure, controlled by the ventilator 10, which provides the desired PEEP level.

Figure 3:
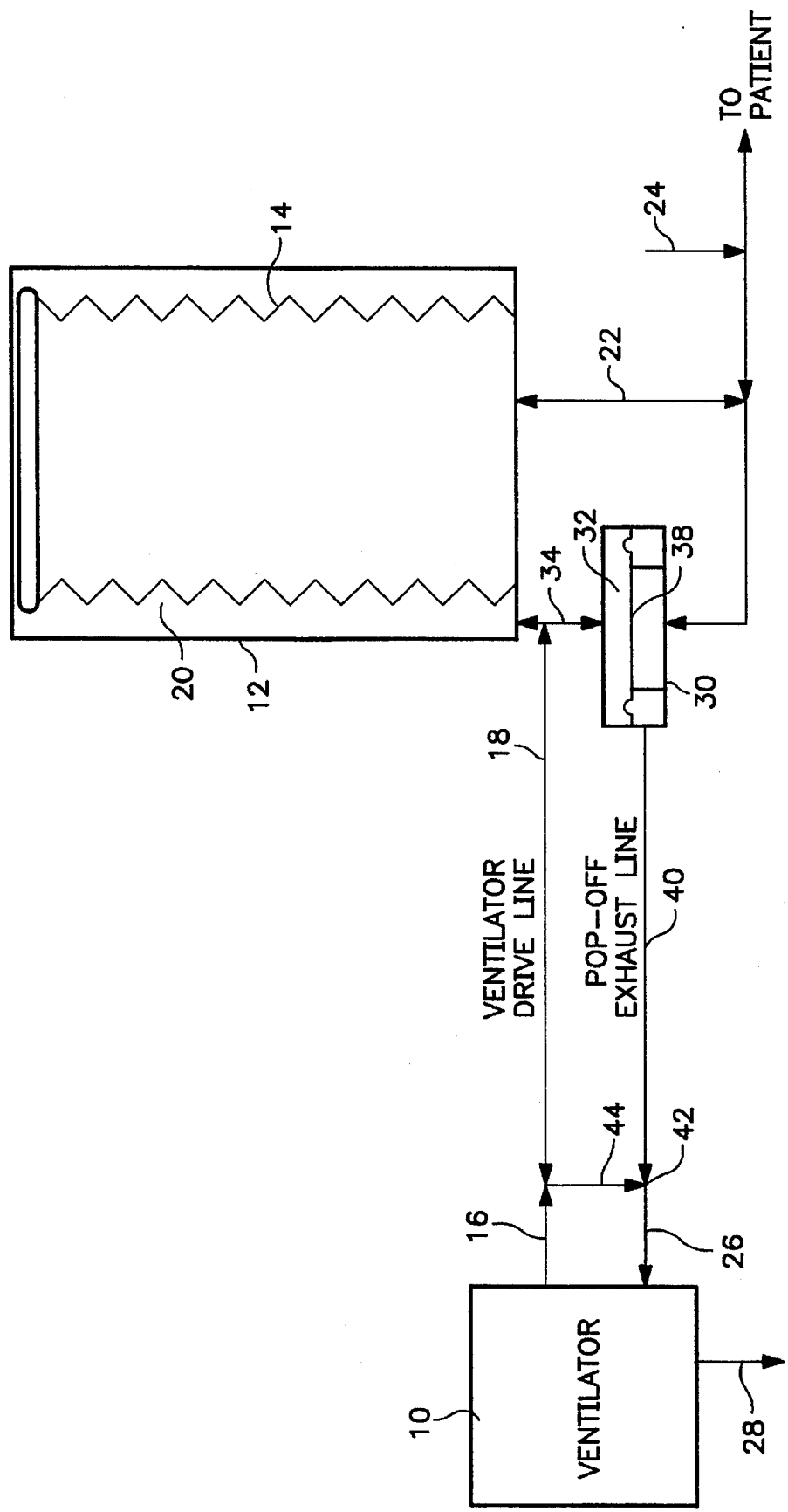
FIG. 3 is a schematic view of a ventilator and bellows system operating in accordance with the preferred mode of operating the present invention.

Turning now to FIG. 3, there is shown a schematic view of a preferred embodiment of the present invention. In the FIG. 3 embodiment, the exhaust line 40 of the pop-off valve 30 is connected to a tee 42. One of the tee connections is to the ventilator drive line 18 via a tee leg 44 and the other of the tee connections is to conduit 26 leading to the exhaust 28 of the ventilator 10. In this embodiment, released gas from ventilator drive line 18 purges the tee leg 44 with every breath. Tee leg 44 is designed to be of sufficient length so as to avoid mixing of pop-off gas from pop-off exhaust line 40 with gas contained in the ventilator drive line 18.

The preferred configuration effectively isolates ventilator drive line 18 from contamination by the "dirty" gas contained in pop-off exhaust line 40. However, pneumatic communication between ventilator drive line 18 and pop-off exhaust line 18 is maintained in accordance with the spirit of the_invention. Inasmuch as the pop-off flow is laden with anesthetic and considered "dirty", it is now desirable to connect the ventilator exhaust line 28 to a scavenging system.

While the present invention has been set forth in terms of a specific embodiment, it will be understood that the ventilator and bellows system herein disclosed may be altered or modified by those skilled in the art to other configurations. Accordingly, the invention is to be broadly construed and limited only by the scope and spirit of the claims appended hereto.

I claim:

1. A ventilator system for providing a breath to a patient and for receiving exhaled gases from the patient, said system comprising a ventilator, a bellows canister containing a compressible bellows, a conduit fluidly connecting said ventilator to said bellows canister, said ventilator supplying a quantity of drive gas through said conduit to compress said bellows within said canister to provide a breath to the patient, means to vent said conduit to relieve the pressure within said bellows container to allow exhaled gasses from the patient to enter the interior of said bellows, a pop-off valve, said pop-off valve having a control chamber communicating with the pressure in said conduit and an exhaust chamber communicating with the gasses exhaled from the patient, said pop-off valve being responsive to the differential pressures between said control chamber and said exhaust chamber to open said pop-off valve to exhaust gases from the patient through said exhaust chamber through an exhaust outlet, the improvement comprising means to control the pressure in said exhaust outlet to a variable positive pressure above atmospheric pressure.

2. A ventilator system as defined in claim 1 wherein said means to control the pressure in said exhaust outlet comprises means to provide a positive pressure to said exhaust conduit by said ventilator.

3. A ventilator system as defined in claim 1 wherein said means to control the pressure in said exhaust outlet comprises means to provide a positive control pressure to said exhaust outlet tracking the pressure of said drive gas in said conduit.

4. A ventilator system as defined in claim 3 wherein said means to control pressure in said exhaust outlet comprises a conduit connecting said exhaust outlet to said conduit.

5. A ventilator system as defined in claim 3 wherein said means to control pressure in said exhaust outlet further comprises a tee conduit of a predetermined length preventing said gas from said exhaust conduit from mixing with the drive gas in said conduit.

6. A ventilator system as defined in claim 5 wherein said means to control pressure in said exhaust outlet further comprises means to flush said tee conduit with drive gas from said conduit.

7. A ventilator system for providing a breath to a patient fluidly connected to a patient circuit during an inspiratory cycle and for receiving exhaled gases from the patient during an exhalation cycle, said system comprising a ventilator, a bellows canister containing a compressible bellows, a drive conduit fluidly connecting said ventilator to said bellows canister, said ventilator supplying a quantity of gas through said drive conduit to compress said bellows within said canister to provide a breath to the patient, said ventilator further having means to provide and maintain a selectable positive pressure within the patient circuit during the expiratory cycle, means to vent said drive conduit to relieve the pressure within said bellows container to allow exhaled gasses from the patient to enter the interior of said bellows, a pop-off valve, said pop-off valve having a control chamber communicating with the pressure in said drive conduit and an exhaust chamber communicating with the gasses exhaled from the patient and a flexible diaphragm separating said chambers, said pop-off valve being responsive to the differential pressures between said control chamber and said exhaust chamber to move said diaphragm to open said pop-off valve to exhaust gases from the patient through said exhaust chamber through an exhaust outlet, and means to control the pressure in said exhaust outlet to track said selectable positive pressure within the patient circuit.

8. A ventilator system as defined in claim 7 wherein said means to provide and maintain a selectable positive pressure within the patient circuit comprises establishing a gas pressure signal from said ventilator.

9. A ventilator system as defined in claim 8 wherein said gas pressure signal is communicated to said control chamber of said pop-off valve and to said exhaust outlet of said pop-off valve.

10. A ventilator system as defined in claim 9 wherein said gas pressure signal is communicated to said exhaust outlet through said drive conduit.

11. A ventilator system as defined in claim 10 wherein said gas pressure signal is communicated to said exhaust outlet by a conduit joining said drive conduit and said exhaust outlet.

12. A ventilator system as defined in claim 11 wherein said conduit joining said drive conduit and said exhaust conduit is of a predetermined length to prevent gas from said exhaust outlet from mixing with the drive gas in said drive conduit.

13. A ventilator system as defined in claim 12 wherein said drive gas flushes exhaust gasses in said conduit away from said drive conduit during each inhalation cycle of said ventilator.

14. A method of controlling a pop-off valve used in a medical ventilation system supplying a breathing gas to a patient connected to a patient breathing circuit comprising the steps of:

providing a medical ventilator to administer a breath to a patient during an inhalation cycle and to receive exhaled breath from the patient during an exhalation cycle;

establishing and maintaining a positive, controllable pressure in the patient circuit during at least one of the exhalation and inhalation cycles, providing a pop-off valve in communication with the patient circuit to vent excess pressure through an exhaust conduit, and controlling the pressure in the exhaust conduit of the pop-off valve at a pressure above atmospheric pressure.

15. A method as defined in claim 14 wherein said step of controlling the pressure in the exhaust conduit comprises controlling that pressure to track the positive, controllable pressure administered to the patient circuit.

16. A method as defined in claim 14 wherein the step of establishing and maintaining a positive controllable pressure in the patient circuit is during the exhalation cycle.

* * * * *